United States Patent [19]

Franck et al.

[11] 4,140,621

[45] Feb. 20, 1979

[54] MAINTAINING OR INCREASING THE ISOBUTANE CONTENT OF A CUT SUBJECTED TO SELECTIVE HYDROGENOLYSIS

[75] Inventors: Jean-Pierre Franck, Bougival; Jean-Francois Le Page, Rueil Malmaison; Germain Martino, Poissy; Jean Miquel, Paris, all of France

[73] Assignee: Institut Francais du Petrole, Rueil-Malmaison, France

[21] Appl. No.: 835,076

[22] Filed: Sep. 20, 1977

[30] Foreign Application Priority Data

Sep. 20, 1976 [FR] France ................. 76 28135

[51] Int. Cl.² ................. C07C 9/08; B01J 27/04
[52] U.S. Cl. ................. 208/58; 252/466 PT; 208/68; 208/96; 208/112; 208/138; 208/141; 260/676 R; 260/683.65

[58] Field of Search ................. 208/110–112, 208/57–61, 85, 87, 89, 96, 138, 68, 141; 260/676, 683.65, 676 R

[56] References Cited

U.S. PATENT DOCUMENTS

| 3,642,925 | 2/1972 | Rausch | 260/668 A |
| 3,772,397 | 11/1973 | Rausch | 260/683.65 X |
| 3,788,975 | 1/1974 | Donaldson | 208/60 |
| 3,879,484 | 4/1975 | Pollitzer | 260/668 A |

Primary Examiner—Delbert E. Gantz
Assistant Examiner—G. E. Schmitkons
Attorney, Agent, or Firm—Millen & White

[57] ABSTRACT

A saturated hydrocarbon charge containing both butane and isobutane is subjected to selective hydrogenolysis in the presence of a catalyst comprising a specific carrier and 0.1 - 10 % b.w. of rhodium. Butane is thus selectively converted to ethane and propane, while isobutane is preserved or formed and can be recovered from the reaction product.

11 Claims, No Drawings

MAINTAINING OR INCREASING THE ISOBUTANE CONTENT OF A CUT SUBJECTED TO SELECTIVE HYDROGENOLYSIS

The present invention concerns a process for converting by hydrogenolysis a charge containing at least both butane and isobutane, and consisting, for example, of saturated paraffinic and/or naphthenic hydrocarbons with at least 4 and at most 7 carbon atoms per molecule; the hydrogenolysis results in the preferential production of ethane and, although to a minor extent, of propane, with simultaneous production of isobutane and/or without destruction of the isobutane of the charge. Thus, the present invention also concerns a process for increasing the isobutane content of a saturated hydrocarbon cut.

When satisfactorily conducted, the hydrogenolysis reactions allow for the production of satisfactory yields of ethane and propane, which products are subject to a great demand, since they can be converted to ethylene and propylene by steam-cracking, these two olefins being important petrochemical starting materials. However the charges usually employed for hydrogenolysis to produce ethane and propane contain from 4 to 10 carbon atoms per molecule, these molecules consisting not only of linear paraffins but also of branched paraffins and naphthenes. These charges thus not only contain materials convertible to ethane and, in lower proportion, to propane, but also materials with side-chains, particularly isobutane, which, during the hydrogenolysis reaction, are cracked to products other than ethane and propane, particularly low value products such as methane. It should then be of high interest to have a hydrogenolysis process available, in which isobutane initially contained in the charge or formed during the hydrogenolysis is maintained substantially unconverted and in which the hydrocarbons of the charge with a side-chain, which cannot be converted to ethane and propane, are converted in a major proportion to isobutane, since isobutane is a valuable product whose demand for alkylate production in high. The present invention precisely results in by the use of specific catalysts, on the one hand, a very high selectivity to ethane and propane, by hydrogenolysis of a $C_4$ - $C_7$ cut, and on the other hand, to an increase in the isobutane content of the initial charge.

The non-conversion of isobutane also permits a saving in hydrogen which otherwise should be lost by this non-selective conversion.

It is to be noted that any isobutane recovered in the hydrogenolysis effluent may be at least partly recycled to the hydrogenolysis zone to eliminate heat produced in that zone.

The hydrogenolysis reaction will be carried out in the following operating conditions:

- the working temperature will be selected between 200 and 400° C; it can be operated advantageously between 230 and 290° C.
- the total pressure will be selected between 1 and 120 bars, preferably between 5 and 50 bars,
- the space velocity will range between 0.1 and 100 liters of liquid charge per liter of catalyst per hour,
- the hydrogen/hydrocarbon ratio will range between 0.5 and 50 (in moles), preferably between 1 and 20 (in moles).

It is operated in the presence of a catalyst necessarily comprising (a) a porous carrier on an alumina or silica base, (b) from 0.1 to 10% b.w., particularly 0.3 to 4% b.w., of rhodium with respect to the carrier. The preferred carrier is alumina (for example alumina of high specific surface, higher than 100 or even than 150 m²/g, for example $\gamma$ cubic or $\eta$ alumina). 0.2 to 3% or preferably 0.3 to 2% of rhodium b.w. of the carrier may be usefully employed.

The catalyst may be prepared according to conventional methods consisting of impregnating the carrier with a solution of a rhodium compound. It is usually terminated with calcination at, for example, between about 500 and 1000° C. preferably in the presence of free oxygen, for example by scavenging with air; the calcination is not mandatory; in case no calcination occurs, the catalyst is directly reduced.

Rhodium may be used in any known form, for example as chloride, bromide, sulfate or sulfide or also as ammonium chlororhodate.

A particular example of application of the invention is the treatment of an olefinic $C_4$ cut from a steam-cracking zone, which treatment comprises extracting butadiene from the olefinic cut, hydrogenating the resulting cut in one or two steps to convert the butenes and isobutenes of the olefinic cut to butane and isobutane and hydrogenolyzing the resulting cut, according to the process of the invention, to convert butane to ethane and propane, without substantially converting isobutane. At the outlet from the hydrogenolysis, the product is subjected to cooling and the $C_4$ cut which contains less than 5% b.w. of n-butane is condensed. A portion of the condensate may be recycled to the reactor, to eliminate the reaction heat, while the other portion may be discharged from the plant to be stored or to be fed to the alkylation plant. The recycling rate is so calculated that the ratio n-butane/butane + isobutane at the inlet of the reactor be lower than 0.3; the hydrogenolysis catalyst bed may be usefully divided into 2 or 3 sections between which a fraction of the recycled liquid may be injected. The gaseous fraction containing unreacted hydrogen, ethane, methane, propane and also a variable butane fraction, depending on the conditions of temperature and partial pressures in the separator, may be passed, without further separation, to the ethane pyrolysis furnaces.

The recycling of isobutane to the hydrogenolysis reactor permits a lowering of the temperature produced by the n-butane transformation, by utilizing the sensible heat of the reactant, the reaction products and, above all, the recycled isobutane. It is preferred to feed the recycled isobutane as liquid between the hydrogenolysis beds, so as to eliminate a portion of the heat produced by the reaction by utilizing the latent heat of vaporization of the isobutane.

The first two examples illustrate the present invention; they have been carried out with the same catalyst on the base of transition alumina in the form of balls of 1.5 – 2.5 mm diameter with a specific surface of 190 m² per gram, a grain density of 1.27, a structure density of 3.35 and a pore volume of 0.49 cc per gram.

This catalyst contained 2% b.w. of rhodium.

EXAMPLE 1

The starting material, or charge, is a $C_4$ cut whose composition is given in Table I, also giving the composition of the product discharged from the hydrogenolysis zone.

The operating conditions are the following:
- pressure: 30 bars

- temperature: 270° C.
- volume of liquid charge/volume of catalyst/hour: 2
- molar ratio H$_2$/hydrocarbons: 6

TABLE I

| % BY WEIGHT | CHARGE | PRODUCT |
|---|---|---|
| methane | 0 | 6.04 |
| ethane | 0 | 60.89 |
| propane | 1.73 | 10.45 |
| isobutane | 25.60 | 21.02 |
| n-butane | 72.10 | 1.44 |
| i-pentane | 0 | 0 |
| n-pentane | 0.55 | 0 |
| others | — | 0.16 |

The very high selective conversion of normal butane, which attains 95% b.w., is remarkable as compared with the hydrogenolysis rate of isobutane which is by far lower, only 17.8% b.w.; there is thus a selective hydrogenolysis of normal butane, increasing the isobutane proportion. High yields of ethane are obtained, amounting to 80.9% b.w. with respect to the converted butanes. A lower yield of propane amounting to 13.9% b.w. of the converted butanes, is attained.

EXAMPLE 2

The charge is light gasoline whose composition is given in Table II, also reporting the composition of the product discharged from the hydrogenolysis zone.

The operating conditions are:
- pressure: 30 bars
- temperature: 285° C.
- volume of liquid charge/volume of catalyst/hour: 2
- molar ratio H$_2$/hydrocarbons: 7

TABLE II

| % BY WEIGHT | CHARGE | PRODUCT |
|---|---|---|
| methane | 0 | 14.38 |
| ethane | 0 | 41.98 |
| propane | 0.06 | 19.63 |
| i-butane | 0.06 | 16.81 |
| n-butane | 0.83 | 1.72 |
| pentane | 34.89 | 4.55 |
| hexanes | 43.05 | |
| heavier than C$_6$ (C$_6^+$) | 21.11 | 0.83 |

The results given in Table II show the preferential production of isobutane by selective hydrogenolysis of the C$_5^+$ hydrocarbons contained in the light gasoline. In fact, the charge subjected to hydrogenolysis contains only traces of isobutane (0.06% b.w.), while the product contains 16.8% thereof.

Nearly all the charge (93.6% b.w.) has been converted to saturated hydrocarbons with a molecular weight equal to or lower than that of the butanes.

This example shows that, when operating in the presence of the catalyst according to the invention, at a correct temperature, even a charge of low n-butane and isobutane content is converted to isobutane.

It is also remarkable that the yield of ethane was high (44.4% b.w. of the converted hydrocarbons) and the yield of propane slightly lower (20.7% b.w.).

EXAMPLE 3

The starting material is a steam-cracking C$_4$ cut from which butadiene has been extracted and which has the composition stated in the following Table III. Hydrogen is used as pure hydrogen containing less than 5 parts of carbon monoxide and oxygen per million. The operation is a continuous one. In a first step operated in a reactor at a stationary concentration of olefins, the charge is hydrogenated in the presence of a homogeneous catalyst (10 ppm of nickel octoate reduced with triethyl aluminum). The operation is conducted at 120° C under a total pressure of 25 bars; the H$_2$/hydrocarbon ratio is 1.8 at the inlet of the reactor. The partially hydrogenated product is passed into a reactor of the concentration gradient type containing a catalyst based on 0.6% Pd by weight deposited on alumina of 60 m$^2$/g specific surface; the hydrogenation is terminated therein to obtain a product whose composition is given in Table III, second column. The operation is conducted at an average temperature of 130° C. on this second catalyst bed, at a space velocity of 2 (expressed as liters of liquid charge per liter of catalyst per hour).

After this hydrogenation, the mixture of hydrogen and hydrocarbons is reheated to 250° C. to be fed to a second reactor of the concentration gradient type where has been placed a hydrogenolysis catalyst based on 0.6% Rh by weight on γ alumina of specific surface equal to 200 m$^2$/g. The results at the end of the hydrogenolysis are given in Table IV; they concern only the hydrocarbons. The operation was conducted at 250° C. It was found that initial n-butane or that formed by hydrogenation of 1-butene or cis and trans 2-butenes and the traces of butadiene hydrogenolyzed at more than 90% b.w., while isobutane (either initially present in the charge or obtained by hydrogenation of isobutene) was converted in a porportion lower than 5% b.w.; it was further observed that ethane was the main product of the transformation; propane and methane were also obtained in lower proportion. The first balance (column 1) was obtained after 30 h or run and the second balance (column 2) after 250 h of continuous run. The pressure applied in this example was 25 bars and the space velocity in the bed of hydrogenolysis catalyst was 1 (liters of liquid charge/liter of catalyst/hour). The ratio H$_2$/n-butane by mole was 1.5.

TABLE III

| COMPOSITION OF THE HYDROGENATION CHARGE | % BY WEIGHT | COMPOSITION OF THE HYDROCARBON EFFLUENT FROM THE HYDROGENATION CHARGE TO HYDROGENOLYSIS (% by weight) |
|---|---|---|
| Isobutane | 0.91 | 47.10 |
| Butane | 2.90 | 52.68 |
| C$_4^+$ paraffins | 0.11 | 0.11 |
| 1-butene | 28.33 | < 5 pm |
| Isobutene | 46.27 | < 5 ppm |
| Trans-2-butene | 11.87 | < 5 ppm |
| Cis 2-butene | 8.54 | < 5 ppm |
| Butadiene | 1.04 | — |

TABLE IV

| (Effluent from the hydrogenolysis) | | |
|---|---|---|
| Time % b.w. Products | 30 h | 250 h |
| Methane | 7.2 | 7.0 |
| Ethane | 33.3 | 33.1 |
| Propane | 10.1 | 10.1 |
| Butane | 2.5 | 2.8 |
| Isobutane | 46.8 | 46.9 |
| C$_4^+$ | 0.1 | 0.1 |
| % molar H$_2$/C$_1$ + C$_2$ + C$_3$ + H$_2$ | 0.27 | 0.25 |

When recycling isobutane to the hydrogenolysis catalyst by feeding back isobutane from the C$_4$ issued from the hydrogenolysis step to the inlet of the hydrogenolysis reactor, at a total VVH of 2, the other conditions being unchanged, it is observed (with a charge containing 74% of isobutane and 26% butane b.w.) that the selectivity of the transformation is good, i.e. isobutane is slightly converted (73.9% b.w. of isobutane at the outlet of the hydrogenolysis) while n-butane is converted at more than 85% b.w. with an ethane and propane (desired products) yield b.w. higher than 91% (3.10% b.w. of butane at the outlet of the hydrogenolysis step).

What we claim is:

1. A process for upgrading the value of an olefinic $C_4$ cut from a stream cracking zone, which process comprises
   (a) extracting butadiene from the olefinic cut,
   (b) hydrogenating the resulting butadiene-depleted olefinic cut to convert the butenes and isobutenes of the olefinic cut to butane and isobutane, and
   (c) hydrogenolyzing the resulting cut from step (b) to convert butane to ethane and propane, without substantially converting isobutane, the hydrogenolysis being conducted in the presence of hydrogen, at a temperature between 200 and 400° C., under a total pressure between 1 and 120 bars, at a space velocity between 0.1 and 100 liters of liquid charge per liter of catalyst per hour, at a molar ratio of hydrogen to hydrocarbons between 0.5 and 50, in the presence of a catalyst consisting essentially of an alumina carrier and a catalytic metallic component consisting essentially of rhodium, the rhodium content being between 0.1 and 10% by weight of the catalyst carrier.

2. A process according to claim 1, wherein the rhodium content is between 0.3 and 4% by weight of the catalyst carrier.

3. A process according to claim 1, wherein isobutane is converted, in step (c), in a proportion of less than 5% by weight.

4. A process according to claim 3, further comprising, at the outlet from the hydrogenolysis, subjecting the product to cooling to condense the $C_4$ cut and recycling at least a portion of the condensate towards the hydrogenolysis step, the recycling rate being adjusted so that the ratio n-butane/butane + isobutane at the inlet of the reactor be lower than 0.3 by weight.

5. A process according to claim 3, further comprising recycling at least a portion of isobutane withdrawn from the hydrogenolysis step to the hydrogenolysis zone.

6. A process according to claim 1, wherein the olefinic $C_4$ cut from the stream-cracking zone contains, after the extraction of butadiene, a major amount of a mixture of 1-butene and isobutene.

7. A process according to claim 1, wherein the hydrogenolysis reaction is conducted at 230–290° C., under a total pressure of 5 – 50 bars and with a hydrogen/hydrocarbon mole ratio of between 1 and 20.

8. A process according to claim 1, wherein the alumina carrier has a specific surface higher than 100 $m^2/g.$, and the rhodium is present in a concentration by weight of 0.2-3%.

9. A process according to claim 1, wherein the alumina carrier has a specific surface higher than 150 $m^2/g.$, and the rhodium is present in a concentration by weight of 0.3-2%.

10. A process according to claim 1, wherein said catalytic metal component consists of rhodium.

11. A process according to claim 1, wherein said catalyst consists of alumina and rhodium.

* * * * *